(12) United States Patent
Jbach et al.

(10) Patent No.: US 10,689,320 B2
(45) Date of Patent: *Jun. 23, 2020

(54) METHOD FOR SEPARATING FORMIC ACID FROM A REACTION MIXTURE BY MEANS OF EXTRACTION

(71) Applicant: OXFA GMBH, Scheßlitz (DE)

(72) Inventors: Hermann Wolf Jbach, Bischberg (DE); Florian Kohler, Nuremberg (DE); Matthias Schmidt, Erlangen (DE); Gunthard Scholz, Gundelsheim (DE); Martin Dirauf, Ebensfeld (DE)

(73) Assignee: OXFA GMBH, Schesslitz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/318,673

(22) PCT Filed: Jul. 17, 2017

(86) PCT No.: PCT/EP2017/068055
§ 371 (c)(1),
(2) Date: Jan. 17, 2019

(87) PCT Pub. No.: WO2018/015352
PCT Pub. Date: Jan. 25, 2018

(65) Prior Publication Data
US 2019/0248727 A1      Aug. 15, 2019

(30) Foreign Application Priority Data

Jul. 18, 2016   (DE) .................. 10 2016 213 100

(51) Int. Cl.
*C07C 51/48* (2006.01)
*B01J 23/00* (2006.01)
(Continued)

(52) U.S. Cl.
CPC .............. *C07C 51/48* (2013.01); *B01J 23/002* (2013.01); *B01J 38/14* (2013.01); *C07C 51/44* (2013.01);
(Continued)

(58) Field of Classification Search
CPC ......... C07C 51/44; C07C 51/48; C07C 51/50; C07C 53/02; B01J 23/002; B01J 38/14
See application file for complete search history.

(56) References Cited

U.S. PATENT DOCUMENTS

2013/0245319 A1* 9/2013 Bosmann ................ C07C 51/23
562/531

FOREIGN PATENT DOCUMENTS

| DE | 10 2011 077 232 A1 | 3/2012 |
| EP | 2 473 467 B1 | 9/2013 |
| WO | 2013/092403 A1 | 6/2013 |

OTHER PUBLICATIONS

International Search Report, International Application No. PCT/EP2017/068055 (published under WO 2018/015352), 4 pages (dated Oct. 20, 2017).

(Continued)

*Primary Examiner* — Yate' K Cutliff
(74) *Attorney, Agent, or Firm* — Prismatic Law Group, PLLC

(57) ABSTRACT

The invention relates to a method for separating formic acid from a reaction mixture by means of extraction, wherein, in addition to the formic acid, the reaction mixture comprises a polyoxometalate ion of general formula $[PMo_xV_yO_{40}]^{n-}$ as a catalyst and a solvent that dissolves the catalyst, wherein $6 \leq x \leq 11$, $1 \leq y \leq 6$, $x+y=12$ and $3<n<10$, wherein n, x, and y are each a whole number, wherein the separation occurs via extraction by means of a polar organic extraction agent which extracts the formic acid and the catalyst and which is N-(n-hexadecyl)formamide, N-di-n-acetamide or an N,N-

(Continued)

Figure 1:
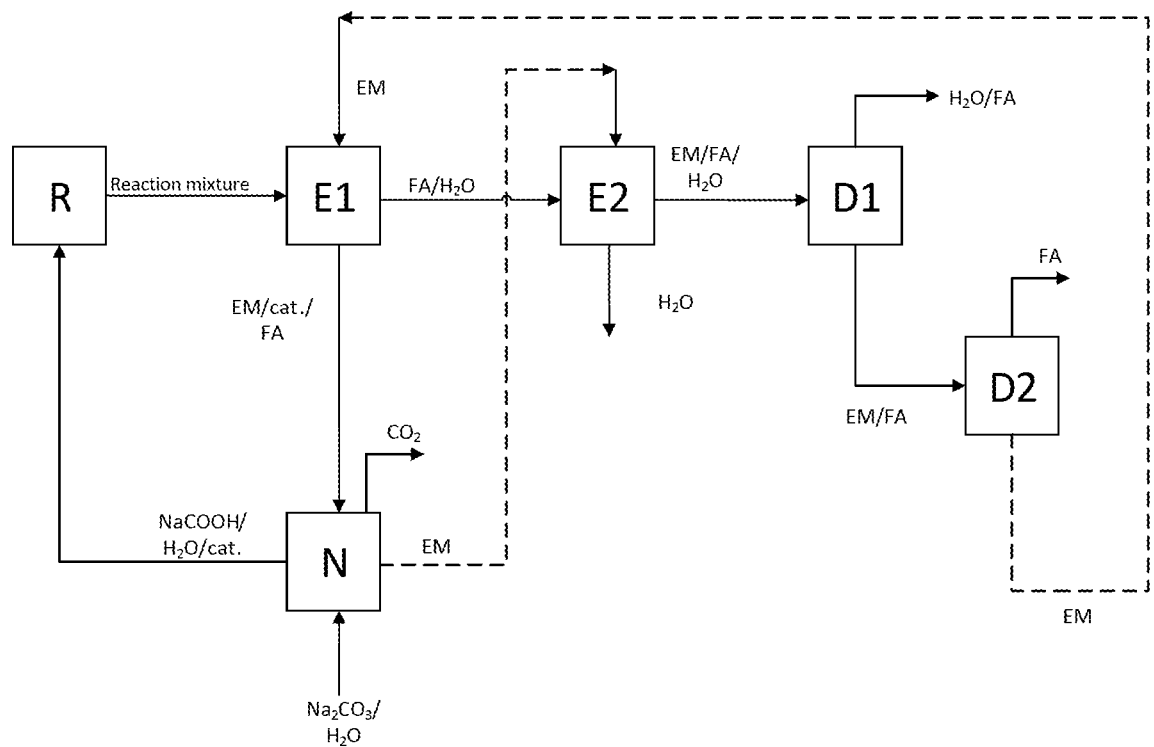

dialkylcarboxamide, wherein the N,N-dialkylcarboxamide forms a phase boundary between the solvent and the extraction agent during mixing with the solvent.

18 Claims, 1 Drawing Sheet

(51) Int. Cl.
    *C07C 53/02*     (2006.01)
    *C07C 51/44*     (2006.01)
    *B01J 38/14*     (2006.01)
    *C07C 51/50*     (2006.01)

(52) U.S. Cl.
    CPC .............. *C07C 51/50* (2013.01); *C07C 53/02* (2013.01); *B01J 2523/51* (2013.01); *B01J 2523/55* (2013.01); *B01J 2523/68* (2013.01)

(56) References Cited

OTHER PUBLICATIONS

Schierbaum et al., "Integriertes Verfahren zur Reinigung von carbonsäurehaltigen Prozeßabwässern," Chemie Ingenieur Technik, vol. 69, pp. 519-523 (1997).

* cited by examiner

METHOD FOR SEPARATING FORMIC ACID FROM A REACTION MIXTURE BY MEANS OF EXTRACTION

This application is a 371 national phase of International Patent Application No. PCT/EP2017/068055 filed Jul. 17, 2017, which claims priority to German Patent Application No. 10 2016 213 100.1 filed Jul. 18, 2016, the content of each of which applications is incorporated herein by reference.

The invention relates to a method for isolating formic acid from a reaction mixture by extraction, wherein the reaction mixture besides the formic acid comprises a polyoxometalate ion of the general formula $[PMo_xV_yO_{40}]^{n-}$ as catalyst and a solvent which dissolves the catalyst, where $6 \leq x \leq 11$, $1 \leq y \leq 6$, $x+y=12$, and $3 < n < 10$, where n, x and y are each an integer. The isolating here is accomplished by extraction by means of a polar organic extractant which extracts the formic acid and the catalyst and which on mixing with the solvent forms a phase boundary between the solvent and the extractant.

Known from DE 10 2011 077 232 A1 and its corresponding EP 2 473 467 B1 is a method for the catalytic generation of formic acid wherein a polyoxometalate ion of the general formula $[PMo_xV_yO_{40}]^{5-}$ serving as catalyst is contacted at a temperature below 120° C. with an alpha-hydroxyaldehyde, an alpha-hydroxycarboxylic acid, a carbohydrate or a glycoside in a liquid solution, where $6 \leq x \leq 11$ and $1 \leq y \leq 6$ and $x+y=12$, where x and y are each an integer. Additionally described in the publication is the possibility of isolating the formic acid thus prepared by means of extraction. To extract the formic acid, the extractant used may be an ether. Besides the formic acid, the catalyst together with the formic acid may be extracted by means of an amide.

It is an object of the present invention to specify an alternative method for isolating formic acid from a reaction mixture by extraction.

The object is achieved by the features of claim 1. Useful embodiments are evident from the features of claims 2 to 13.

Provided in accordance with the invention is a method for isolating formic acid from a reaction mixture by extraction, wherein the reaction mixture besides the formic acid comprises a polyoxometalate ion of the general formula $[PMo_xV_yO_{40}]^{n-}$ as catalyst and a solvent which dissolves the catalyst, where $6 \leq x \leq 11$, $1 \leq y \leq 6$, $x+y=12$ and $3 < n < 10$, where n, x and y are each an integer. The isolating here takes place by extraction, more particularly reactive extraction, by means of a polar organic extractant which extracts the formic acid and the catalyst and which on mixing with the solvent forms a phase boundary between the solvent and the extractant. In the case of reactive extraction, the extractant reacts chemically at least with the formic acid or with the catalyst, in an ion exchange reaction or by forming chemical bonds, for example.

The solvent may be a solvent which as well as the catalyst also dissolves a substrate of the catalyst. The substrate of the catalyst may be an alpha-hydroxyaldehyde, an alpha-hydroxycarboxylic acid, a carbohydrate, a glycoside, or a polymer containing a carbon chain and having at least one OH group bonded repeatedly as a substituent on the carbon chain, and/or having an O, N or S atom present repeatedly in the carbon chain. An alpha-hydroxyaldehyde is any molecule in which an OH group is bonded directly to a C atom, where the C atom of an aldehyde group is also bonded directly to the C atom. An alpha-hydroxycarboxylic acid is any molecule in which an OH group is bonded directly to a C atom, where the C atom of a carboxyl group is also bonded directly to the C atom. An alpha-hydroxyaldehyde and an alpha-hydroxycarboxylic acid may also refer to any substance which comprises an alpha-hydroxyaldehyde or an alpha-hydroxycarboxylic acid. If the substrate itself is in liquid form, the substrate may also be the solvent which dissolves the catalyst.

The extractant is N-(n-hexadecyl)formamide, N-di-n-acetamide or an N,N-dialkylcarboxamide which, for extraction of the catalyst present at a concentration of 1.5 wt % in water, has a partition coefficient at 40° C. for the catalyst that is greater by a factor of at least 7, more particularly by a factor of at least 8, more particularly by a factor of at least 9, more particularly by a factor of at least 10, more particularly by a factor of at least 15, more particularly by a factor of at least 20, more particularly by a factor of at least 25, more particularly by a factor of at least 30, than a partition coefficient for extraction of the formic acid present at a concentration of 5 wt % in water, at 40° C. The partition coefficient K is defined as follows:

$$K = \frac{\text{(concentration of formic acid or catalyst) in the extractant}}{\text{(concentration of formic acid or catalyst) in water}}$$

"Water" here may also refer to the aqueous phase in a two-phase system with the extractant. In the determination of the partition coefficient for the catalyst, for example, the aqueous phase may also comprise formic acid. As a result, the extractant may extract the catalyst more rapidly at the start of the extraction than the formic acid. "More rapidly" here denotes in particular that the weight percentage proportion of catalyst in the catalyst present in total in the reaction mixture passing into the extractant per unit time is greater than the weight percentage proportion of the formic acid in the formic acid present in total in the reaction mixture.

According to Schierbaum B. et al., "Integriertes Verfahren zur Reinigung von carbonsäurehaltigen Prozeβabwässern" [Integrated method for purifying process wastewaters containing carboxylic acid], Chemie Ingenieur Technik (69), 1997, pages 519 to 523, the partition coefficient K of formic acid in a two-phase system composed of N,N-di-n-butylformamide (DBFA) and 5% formic acid in water at a temperature of 40° C. is 2.5. For the catalyst $[PMo_7V_5O_{40}]^{8-}$ (HPA-5), measurements by the inventors show a partition coefficient K of 3284 in a two-phase system comprising DBFA and 1.5% HPA-5 in water. This shows that in this example the partition coefficient for the extraction of the catalyst is greater by a factor of 1313 than the partition coefficient for the extraction of the formic acid.

Before the extraction, the extractant is saturated with the catalyst. This prevents the extraction of the catalyst during the extraction or accomplishes that in the extraction it is only the formic acid that is extracted.

Alternatively, the catalyst extracted together with the formic acid is isolated from the extractant used, after the extraction, by means of precipitation as a salt or by means of a further extraction with a polar further extractant and with a temperature change of the extractant and/or with an increase in the pH of the extractant, and is returned to the reaction mixture. This can prevent a substantial reduction in the concentration of the catalyst in the reaction mixture and maintain a reaction catalyzed by the catalyst in the reaction mixture. For this purpose, for example, the formic acid may first be isolated from the extractant by distillation and thereafter the catalyst may be isolated from the extractant by precipitation as a salt.

By virtue of the method of the invention it is possible to extract the formic acid and at the same time to maintain, at least substantially, the concentration of the catalyst in the reaction mixture. Consequently, the reaction for generating the formic acid can continue to operate in the reaction mixture. It is at least not substantially hindered by the extraction of the formic acid.

With the existing extraction methods in which the catalyst has been extracted together with the formic acid, the catalyst was removed from the reaction mixture, and was then no longer available for further reaction. Since the catalyst is relatively expensive, the method becomes relatively expensive because of the loss of the catalyst and the associated need to supply new catalyst to the reaction mixture, despite the fact that the catalyst is needed only in a small quantity.

The extraction can be carried out in two stages, by extracting the reaction mixture in a first extraction step with a first quantity of the extractant, in particular for a first time, to extract the catalyst, and extracting the reaction mixture in a second extraction step with a second quantity of the extractant, in particular for a second time, to extract the formic acid. The first quantity may be a first portion and the second quantity a second portion of the extractant employed overall. The quantity of the extractant used overall in the method may be from 0.1 times up to three times the quantity of the reaction mixture, based in each case on the weight. The catalyst extracted in the first extraction step is returned to the reaction mixture. The catalyst may be isolated from the extractant used in the first extraction step, after the first extraction step, by means of precipitation as a salt or by means of a further extraction with a polar further extractant and with a temperature change of the extractant used in the first extraction step and/or with an increase in the pH of the extractant used in the first extraction step.

Through the temperature change and/or the increase in the pH, the catalyst present in the extractant can be expelled into the further extractant.

On mixing with the extractant or with the extractant used in the first extraction step, the further extractant forms a phase boundary between the further extractant and the extractant or the extractant used in the first extraction step.

The formic acid may be isolated, by means of distillation or by precipitation as the formate, for example, from the extractant used in the second extraction step.

Relative to the single-stage extraction extracting both the catalyst and the formic acid, this method has the advantage that it permits complete or at least virtually complete extraction of the catalyst from the reaction mixture in the first step, with only formic acid or at least almost only formic acid crossing into the extractant in the second step. The method is able to remove the need to carry out a further separating step with the extract in order to separate the catalyst from the formic acid.

The first time and the second time and also the first quantity of the extractant and the second quantity of the extractant may in each case be identical. Minimal isolation of the formic acid from the reaction mixture in the first extraction step and therefore, possibly, minimal loss of the formic acid, however, can be achieved if the second time is longer than the first time and/or the first quantity is smaller than the second quantity, more particularly if the first time is particularly short and/or the first quantity is particularly small. In each case, the first time and the first quantity ought, however, to be sufficient to allow the extraction of more than 33%, more particularly more than 50%, more particularly more than 80% of the catalyst for extraction in each case from the reaction mixture, or even to enable complete or virtually complete extraction of the catalyst from the reaction mixture. The isolation of relatively pure formic acid from the extractant used in the second extraction step is relatively simple in the case of complete or virtually complete extraction of the catalyst from the reaction mixture having taken place in the first step, because in that case the formic acid is present in the extractant used in the second step without the catalyst or at least almost without the catalyst.

By means of precipitation as a salt, the catalyst may be isolated simultaneously with precipitation of the additionally extracted formic acid as formate.

It is also possible for the polar further extractant to be the solvent, water for example, and/or for the increase in the pH of the extractant or of the extractant used in the first extraction step to take place by addition of a carbonate and/or a hydroxide.

Precipitation as a salt may take place by means of a hydroxide, more particularly KOH or NaOH, or of another base.

The precipitated salt may be supplied to the reaction mixture and dissolved beforehand in the solvent and be adjusted, in particular by means of formic acid, to a pH of the reaction mixture. Alternatively or additionally, the further extractant after the further extraction may be supplied to the reaction mixture and adjusted beforehand, in particular by means of formic acid, to a pH of the reaction mixture. If the catalyst is isolated from the extractant after the extraction, or isolated from the extractant used in the first extraction step after the first extraction step, by means of the further extraction with the polar further extractant, more particularly the solvent, and with a temperature change and/or with an increase in the pH, in particular through addition of a carbonate and/or a hydroxide, in order to be returned to the reaction mixture, then the extractant before the extraction or before the further extraction, or at least the extractant used in the first extraction step, before the first extraction step or before the further extraction, may be admixed with an additive, more particularly with an apolar additive. This facilitates the further extraction by temperature change and/or increase in the pH. The effect of the additive is to change the partition between an organic phase and an inorganic phase on temperature change or change in pH. The additive may be petroleum, a fraction of petroleum, n-hexane, n-octane, n-decane, oleyl alcohol, toluene, dibutyl ether or tri-n-butyl phosphate.

The solvent may be a protic and/or polar solvent, more particularly water or a substrate which can be reacted by means of the catalyst.

One possibility for preventing the extraction of formic acid in the first extraction step, ensuring that in the extraction or in the first extraction step it is only the catalyst that is extracted, is to saturate the extractant used with formic acid before the extraction. In this case it has surprisingly been found that the reactive extraction of the catalyst with an extractant comprising an N,N-dialkylcarboxamide saturated with formic acid is more effective than with the N,N-dialkylcarboxamide not saturated with formic acid.

The N,N-dialkylcarboxamide as extractant may be dipentylformamide, N,N-di-n-butylformamide, N-methyl-N-heptylformamide, N-n-butyl-N-2-ethylhexylformamide or N-n-butyl-N-cyclohexylformamide. N,N-Di-n-butylformamide in particular has proven highly suitable. N,N-Dialkylcarboxamides are especially suitable for reactive extraction of the catalyst.

So that the extraction does not necessarily interrupt a reaction to form formic acid that takes place in the reaction mixture, the extraction may be carried out in each case only with a portion of the reaction mixture, which is returned to the rest of the reaction mixture after the extraction. This may also prevent the amount of formic acid in the reaction mixture increasing to the point where it would inhibit the formation of further formic acid. The formation of formic acid would also be inhibited, however, if the pH of the reaction mixture were to increase too far. During the extraction or during the second extraction step, therefore, the amount of formic acid extracted from the reaction mixture ought only to be such that the pH of the reaction mixture does not rise above 3, more particularly not above 2.5, more particularly not above 2. The extracted catalyst can be supplied to the reaction mixture, by being first supplied to the portion of the reaction mixture, which is then in turn supplied to the rest of the reaction mixture.

In order to isolate the formic acid from the extractant used in the extraction or in the second extraction step, it is possible to carry out a distillation, as for example a flash distillation, or a precipitation as formate, or any desired other method for isolating formic acid from the extractant. Following the isolation of the catalyst and of the formic acid from the extractant, the extractant can be reused. In particular it is possible to circulate the extractant in a continuous operation.

The method of the invention may also comprise catalytic generation of formic acid by means of the catalyst and regeneration of the catalyst reduced in the process, where the catalyst is contacted at a temperature above 70° C., 80° C. or 90° C. and below 160° C., 150° C. or 140° C., more particularly below 120° C., with an alpha-hydroxyaldehyde, an alpha-hydroxycarboxylic acid, a carbohydrate, a glycoside or a polymer containing a carbon chain and having at least one OH group bonded repeatedly as substituent to the carbon chain and/or having an O, N or S atom present repeatedly in the carbon chain, as substrate in the reaction mixture. The catalyst reduced in the process can be returned to its original state by oxidation, where the reaction mixture for this purpose is contacted with a gas comprising a volume fraction of at least 18%, more particularly at least 19%, more particularly at least 20% of oxygen at a gas pressure of at least 2 bar, more particularly at least 3 bar, more particularly at least 4 bar, more particularly at least 5 bar, more particularly at least 6 bar, more particularly at least 7 bar, more particularly at least 8 bar, more particularly at least 9 bar, more particularly at least 10 bar, more particularly at least 11 bar, more particularly at least 12 bar, more particularly at least 13 bar, and at most 33 bar, more particularly at most 28 bar, more particularly at most 24 bar, more particularly at most 19 bar, more particularly at most 18 bar, more particularly at most 17 bar, more particularly at most 16 bar, more particularly at most 15 bar, more particularly at most 14 bar, more particularly at most 13 bar, by means of a mixing apparatus or via a liquid-permeable, gas-impermeable membrane. The mixing apparatus may comprise a static mixer, a reactive mixing pump, a nozzle, more particularly a Venturi nozzle or a spraying nozzle, and/or a gas introduction stirrer. The mixing apparatus may for this purpose consist of at least one of the stated mixing devices or may comprise a plurality thereof or else a plurality of different mixing devices from among those stated.

The inventors of the present patent application have found that the CO and/or $CO_2$ formed in the catalytic reaction of the stated substrates under a limited pressure have an unexpectedly strongly limiting effect on the yield of formic acid and/or on the rate of generation of formic acid. They have further found that the rate of generation of formic acid and/or the yield of formic acid can unexpectedly be boosted significantly if CO and/or $CO_2$ formed in the reaction and passing into the gas are taken off in an amount such that the volume fraction of CO and $CO_2$ together in the gas does not exceed 80%, more particularly 70%, more particularly 60%, more particularly 55%, more particularly 50%, more particularly 45%, more particularly 40%, more particularly 35%, more particularly 30%, more particularly 25%, more particularly 20%. The method can therefore be carried out with sufficient yield using a relatively low pressure of not more than 33 bar, or even not more than 28 bar, or even not more than 24 bar, or even not more than 19 bar, or even not more than 18 bar, or even not more than 17 bar, or even not more than 16 bar, or even not more than 15 bar, or even not more than 14 bar, or even not more than 13 bar. The method, indeed, makes it possible to carry out the oxidation of the catalyst with air in a sufficiently effective way under the pressure specified above. Since the apparatus for implementing the method is required as a result to withstand less pressure, the apparatus can be provided much more cost-effectively than an apparatus for implementing the method known from EP 2 473 467 B1 for the catalytic generation of formic acid.

A gas here refers to a gas or a gas mixture. The "volume fraction of CO and $CO_2$ together" means the sum of the volume fractions of CO and $CO_2$. The catalyst reduced in the reaction to form the formic acid is returned to its original state by oxidation. In the sense of the invention, then, a catalyst is also a substance which is altered by reduction during the method and is returned to its original state by oxidation.

The CO and/or $CO_2$ formed in the reaction and passing into the gas can be taken off in an amount such that the volume fraction of CO and $CO_2$ together in the gas does not exceed 80%, 70%, 60%, 55%, 50%, 45%, 40%, 35%, 30%, 25% or 20% by using fresh gas to replace the gas contacting the solution, or at least a part of this gas, permanently or intermittently, no later than on attainment of this volume fraction of 80%, 70%, 60%, 55%, 50%, 45%, 40%, 35%, 30%, 25% or 20%, or by isolating the CO and/or the $CO_2$ from the gas no later than on attainment of this volume fraction of 80%, 70%, 60%, 55%, 50%, 45%, 40%, 35%, 30%, 25% or 20%. Fresh gas is gas which up to that point has not contacted the solution, has an oxygen content of at least 18%, and in which the volume fraction of CO and $CO_2$ together is lower than in the gas replaced.

Figure 2:
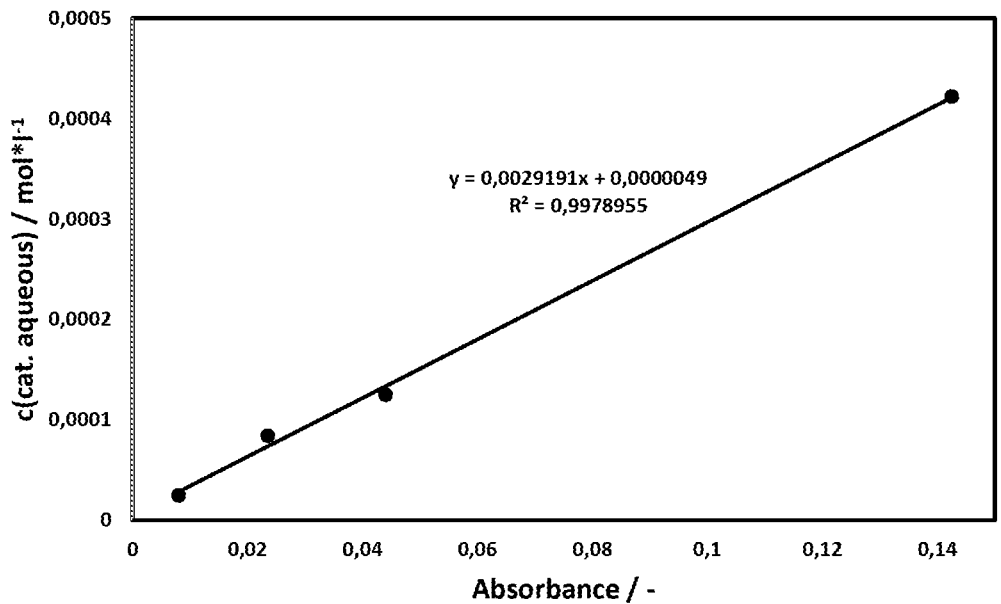

The invention is elucidated in more detail below with an exemplary embodiment. In the drawings:

FIG. 1 shows a schematic representation of a method of the invention,

FIG. 2 shows a calibration line for determining the concentration of the catalyst HPA-5 in an aqueous solution of the catalyst at a wavelength of 435 nm, and In the case of the method according to FIG. 1, the reaction vessel R accommodates a reaction mixture for generating formic acid FA, this mixture comprising glucose and $[PMo_7V_5O_{40}]^{8-}$, for example. Instead of glucose, another alpha-hydroxyaldehyde or another of the substrates identified in claim 15 may also be used. From the reaction vessel R, a portion of the reaction mixture is passed into the first extraction vessel E1, where it is extracted by means of the extractant EM, such as N,N-di-n-butylformamide (DBFA), for example, as organic phase, for about one minute at a temperature of about 30° C. A single-stage extraction is sufficient for this. For this purpose, the first extraction vessel E1 may be constructed, for example, as a mixer-settler apparatus. In order to achieve an extraction of about one minute, the rate at which the extractant EM and the reaction mixture flow through the mixer-settler apparatus must be selected so that the relevant contact time, which takes place in particular in the mixer region of the apparatus, is about one minute. Because of the much higher partition coefficient of the extractant EM for an extraction of the catalyst than for an extraction of the formic acid FA, a short extraction time of this kind is sufficient for extraction of the catalyst. During the extraction, the catalyst in particular, but also a small amount of the formic acid FA, cross into the organic phase.

After the extraction, the extractant EM is passed from the first extraction vessel E1 into a neutralizing vessel N. The extractant EM comprises an apolar additive, such as n-hexane, for example. In the neutralizing vessel N, the extractant is extracted at about 90° C. with an aqueous sodium carbonate solution $Na_2CO_3/H_2O$. During this extraction, sodium formate NaCOOH is formed in the aqueous solution from the formic acid present. $CO_2$ likewise formed escapes in the form of gas. At the same time, owing to the temperature increase and the addition of sodium carbonate, the catalyst crosses into the aqueous phase. The aqueous phase containing the catalyst is passed back into the reaction vessel R, and so the catalyst is available for the further reaction of the substrate.

After the first extraction step has been carried out, the aqueous phase, containing formic acid FA, is passed from the first extraction vessel E1 into a second extraction vessel E2, where it is extracted with the extractant EM for 30 minutes in a multistage extraction, by means of a countercurrent extraction apparatus, for example. The extractant EM may be the extractant remaining after the extraction with the aqueous sodium carbonate solution in the neutralizing vessel N, or fresh extractant, or a mixture of these. In this second extraction step, the formic acid crosses from the aqueous phase into the organic phase. In addition, a small amount of water $H_2O$ may dissolve in the extractant, if the extractant is not already saturated with water. After the second extraction step, the extractant EM, with formic acid and optionally water $H_2O$ dissolved therein, is passed into a first distillation apparatus D1, in which formic acid FA and primarily water $H_2O$ are isolated. This formic acid-water mixture may be used, for example, to acidify the aqueous catalyst solution originating from the neutralizing vessel before this solution is added to the reaction mixture. Acidifying the catalyst solution is advantageous in order to prevent the pH of the reaction mixture in the reaction vessel rising to more than 3, more than 2.5 or more than 2. Any such increase would lead to a reduction in the reaction rate for the generation of the formic acid.

The distillation may be a relatively straightforward flash distillation. The residue from the first distillation in the first distillation apparatus D1 may be passed into a second distillation apparatus D2, where the formic acid is isolated from the extractant EM in a second distillation, which is a second flash distillation, for example. The remaining extractant EM can be passed for extraction into the first extraction vessel E1. There it can be used exclusively or together with fresh extractant EM for implementing the first step of the extraction.

The partition coefficient, for the catalyst HPA-5, for example, may be determined in accordance with the following example:

In a separating funnel, 40 g of N,N-di-n-butylformamide were extracted by shaking with 40 g of an aqueous phase containing 10 wt % formic acid, and with different concentrations of the catalyst HPA-5 in each case, and then left to stand at 40° C. for a week. By this means, complete phase separation was achieved. The phases were then each separated and weighed and the respective concentration of HPA-5 in the aqueous phase was measured by means of a photometer at 435 nm. The partition coefficient K was calculated according to the following formula:

$$K_{HPA\text{-}5} = \frac{\text{concentration of } HPA\text{-}5 \text{ in N,N-di-n-butylformamide}}{\text{concentration of } HPA\text{-}5 \text{ in the aqueous phase}}$$

The resulting partition coefficients at 40° C. are evident from the following table:

| | Extractant | c(cat, start) [wt %] | c(FA, aqueous) [wt %] | c(cat, a) [mol/m] | c(cat, org.) [mol/l] | $K_{HPA\text{-}5}$ |
|---|---|---|---|---|---|---|
| 1 | DBFA | 1.5 | 0 | $2.25*10^{-6}$ | $7.39*10^{-3}$ | 3284 |
| 2 | DBFA | 1.5 | 1 | $2.72*10^{-6}$ | $7.42*10^{-3}$ | 2727 |
| 3 | DBFA | 1.5 | 10 | $3.18*10^{-6}$ | $7.05*10^{-3}$ | 2216 |

The abbreviations here have the following meanings:
DBFA: N,N-di-n-butylformamide; c(cat,start): concentration of the catalyst HPA-5 at the start of the experiment; c(FA, aqueous): concentration of formic acid in the aqueous phase; c(cat,a): concentration of the catalyst in the aqueous phase; c(cat,org): concentration of the catalyst in the organic phase; $K_{HPA\text{-}5}$: partition coefficient K in accordance with the formula above.

The corresponding calibration line for determining the concentration of the catalyst in the aqueous phase after the extraction with DBFA is shown in FIG. 2. In the figure, c(cat, aqueous) is the concentration of the catalyst in the aqueous phase after the phase separation.

Further experiments showed that the phase separation with an aqueous phase comprising formic acid as well as the catalyst is accelerated relative to a phase separation with a purely aqueous solution of the catalyst.

LIST OF REFERENCE SYMBOLS

R reaction vessel
FA formic acid
EM extractant
E1 first extraction vessel
E2 second extraction vessel
D1 first distillation apparatus
D2 second distillation apparatus
N neutralizing vessel
$H_2O$ water
$Na_2CO_3$ sodium carbonate
NaCOOH sodium formate

The invention claimed is:
1. A method for isolating formic acid from a reaction mixture by extraction, wherein the reaction mixture besides the formic acid comprises a polyoxometalate ion of the general formula $[PMo_xV_yO_{40}]^{n-}$ as catalyst and a solvent which dissolves the catalyst, where $6 \leq x \leq 11$, $1 \leq y \leq 6$, $x+y=12$, and 3<n<10, where n, x and y are each an integer, where the isolating is accomplished by extraction by means of a polar organic extractant which extracts the formic acid and the catalyst and which is N—(N-hexadecyl)formamide, N-di-n-acetamide or an N,N-dialkylcarboxamide, where the N,N-dialkylcarboxamide on mixing with the solvent forms a phase boundary between the solvent and the extractant, where the extractant is one which, for extraction of the catalyst present at a concentration of 1.5 wt % in water, has a partition coefficient for the catalyst at 40° C. that is greater by a factor of at least 7 than a partition coefficient for extraction at 40° C. of the formic acid present at a concentration of 5 wt % in water, where the extractant before the extraction is saturated with the catalyst or where the catalyst extracted together with the formic acid is isolated from the extractant after the extraction by means of precipitation as a salt or by means of a further extraction with a polar further extractant and with a temperature change of the extractant and/or with an increase in the pH of the extractant, and is returned to the reaction mixture.

2. The method as claimed in claim 1, wherein the extraction is carried out in two stages, by extracting the reaction mixture in a first extraction step with a first quantity of the extractant in order to extract the catalyst and extracting the reaction mixture in a second extraction step with a second quantity of the extractant in order to extract the formic acid, where the catalyst extracted in the first extraction step is returned to the reaction mixture, where the catalyst is isolated from the extractant used in the first extraction step, after the first extraction step, by means of precipitation as a salt or by means of a further extraction with a polar further extractant and with a temperature change of the extractant used in the first extraction step and/or with an increase in the pH of the extractant used in the first extraction step.

3. The method as claimed in claim 2, wherein the first quantity is smaller than the second quantity and/or the extraction with the first quantity of the extractant takes place for a first time and the extraction with the second quantity of the extractant takes place for a second time and the second time is longer than the first time.

4. The method as claimed in claim 1, wherein the catalyst by means of the precipitation as a salt is isolated simultaneously with precipitation of the extracted formic acid as a formate, or wherein the polar further extractant is the solvent and/or the increase in the pH takes place by addition of a carbonate and/or a hydroxide.

5. The method as claimed claim 1, wherein the precipitation as a salt takes place by means of a hydroxide or of another base.

6. The method as claimed in claim 1, wherein the precipitated salt is supplied to the reaction mixture and dissolved beforehand in the solvent and adjusted to a pH of the reaction mixture, and/or the further extractant after the further extraction is supplied to the reaction mixture and adjusted beforehand to a pH of the reaction mixture.

7. The method as claimed in claim 1, wherein the extractant before the extraction or before the further extraction, or at least the extractant used in the first extraction step, before the first extraction step or before the further extraction, is admixed with an additive and the catalyst is isolated from the extractant after the extraction, or from the extractant used in the first extraction step after the first extraction step, by means of the further extraction with the polar further extractant and with the temperature change and/or the increase in the pH.

8. The method as claimed in claim 7, wherein the additive is petroleum, a fraction of petroleum, n-hexane, n-octane, n-decane, oleyl alcohol, toluene, dibutyl ether or tri-n-butyl phosphate.

9. The method as claimed in claim 1, wherein the solvent is a protic and/or polar solvent.

10. The method as claimed in claim 1, wherein the N,N-dialkylcarboxamide is dipentylformamide, N,N-di-n-butylformamide, N-methyl-N-heptylformamide, N-n-butyl-N-2-ethylhexylformamide or N-n-butyl-N-cyclohexylformamide.

11. The method as claimed in claim 1, wherein the extraction is carried out in each case only with a portion of the reaction mixture, which after the extraction is returned to the rest of the reaction mixture.

12. The method as claimed in claim 1, wherein the amount of formic acid extracted from the reaction mixture in the second extraction step is only such that the pH of the reaction mixture does not rise above 3.

13. The method as claimed in claim 1, wherein the method comprises catalytic generation of formic acid by means of the catalyst and regeneration of the catalyst reduced in the process, where the catalyst is contacted at a temperature between 70° C. and 160° C. with an alpha-hydroxyaldehyde, an alpha-hydroxycarboxylic acid, a carbohydrate, a glycoside or a polymer containing a carbon chain and having at least two OH groups bonded as substituents to the carbon chain and/or having an O, N or S atom present repeatedly in the carbon chain, as substrate in the reaction mixture, where the catalyst reduced in the process is returned to its original state by oxidation, where the reaction mixture for this purpose is contacted with a gas comprising a volume fraction of at least 18% of oxygen at a gas pressure in a range of 2 bar to 33 bar, by means of a mixing apparatus or via a liquid-permeable, gas-impermeable membrane, where CO and/or $CO_2$ formed in the reaction and entering the gas are taken off in a quantity such that the volume fraction of CO and $CO_2$ together in the gas does not exceed 80%.

14. The method of claim 5, wherein the hydroxide is KOH or NaOH.

15. The method of claim 6, wherein the adjusting of the solvent with the precipitated salt dissolved therein and/or of the further extractant to the pH of the reaction mixture is by means of formic acid.

16. The method of claim 7, wherein the admixed additive is a polar additive, the polar further extractant is the solvent, and/or the increase in the pH is by addition of a carbonate and/or a hydroxide.

17. The method of claim 9, wherein the protic and/or polar solvent is water or a substrate which can be reacted by means of the catalyst.

18. The method of claim 12, wherein the amount of formic acid extracted from the reaction mixture in the second extraction step is only such that the pH of the reaction mixture does not rise above 2.5.

* * * * *